US010152633B2

(12) United States Patent
Tomimori et al.

(10) Patent No.: US 10,152,633 B2
(45) Date of Patent: Dec. 11, 2018

(54) LINE-OF-SIGHT DETECTION DEVICE AND LINE-OF-SIGHT DETECTION METHOD

(71) Applicant: FUJITSU LIMITED, Kawasaki-shi, Kanagawa (JP)

(72) Inventors: Hideki Tomimori, Kawasaki (JP); Satoshi Nakashima, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 7 days.

(21) Appl. No.: 15/651,099

(22) Filed: Jul. 17, 2017

(65) Prior Publication Data
US 2018/0046842 A1 Feb. 15, 2018

(30) Foreign Application Priority Data

Aug. 10, 2016 (JP) .................................. 2016-157681

(51) Int. Cl.
G06K 9/00 (2006.01)
G06F 3/01 (2006.01)
(Continued)

(52) U.S. Cl.
CPC ............ G06K 9/0061 (2013.01); A61B 3/113 (2013.01); G06F 3/00 (2013.01); G06F 3/013 (2013.01); G06K 9/00 (2013.01); G06K 9/00604 (2013.01)

(58) Field of Classification Search
None
See application file for complete search history.

(56) References Cited

U.S. PATENT DOCUMENTS 8,447,072 B2 * 5/2013 Takahashi .............. G08G 1/167
382/103
9,521,325 B2 * 12/2016 Yu ...................... G06K 9/00604
(Continued)

FOREIGN PATENT DOCUMENTS

EP 2930656 A1 10/2015
EP 3158921 A1 4/2017
(Continued)

OTHER PUBLICATIONS

Morimoto, Mimica et al.,Eye gaze tracking techniques for interactive applications, Computer Vision and Image Understanding, vol. 98, Issue 1, Apr. 2005, pp. 4-24, Available online: https://doi.org/10.1016/j.cviu.2004.07.010.*
(Continued)

Primary Examiner — Tahmina Ansari
(74) Attorney, Agent, or Firm — Fujitsu Patent Center

(57) ABSTRACT

When a plurality of candidate corneal reflections are extracted from an image of a person, a line-of-sight detection device calculates a movement vector of a reflection location on the basis of the candidate corneal reflection extracted from a first image and a second image, calculates a movement vector of a reference point on the person on the basis of the reference point extracted from the first image and the second image, identifies a corneal reflection from among the plurality of candidate corneal reflections on the basis of the movement vector of the reflection location and the movement vector of the reference point so as to identify a location of the corneal reflection, and extracts a location of a pupil from the image, and calculates a line of sight of the person on the basis of the identified location of the corneal reflection and the extracted location of the pupil.

15 Claims, 14 Drawing Sheets

(51) Int. Cl.
*A61B 3/113* (2006.01)
*G06F 3/00* (2006.01)

(56) References Cited

U.S. PATENT DOCUMENTS

| | | | |
|---|---|---|---|
| 9,524,446 B2* | 12/2016 | Yoshioka | G06K 9/52 |
| 9,910,846 B2* | 3/2018 | Taguchi | G06F 3/0237 |
| 2004/0174496 A1* | 9/2004 | Ji | G06F 3/013 |
| | | | 351/209 |
| 2005/0024586 A1* | 2/2005 | Teiwes | A61B 3/113 |
| | | | 351/209 |
| 2009/0015788 A1* | 1/2009 | Knaan | A61B 3/113 |
| | | | 351/209 |
| 2018/0046842 A1* | 2/2018 | Tomimori | G06F 3/013 |

FOREIGN PATENT DOCUMENTS

| | | |
|---|---|---|
| JP | 2005-296383 | 10/2005 |
| JP | 2006-167256 | 6/2006 |
| JP | 2012-019931 | 2/2012 |
| JP | 2012-239550 | 12/2012 |

OTHER PUBLICATIONS

Y. Ebisawa and K. Fukumoto, "Head-Free, Remote Eye-Gaze Detection System Based on Pupil-Corneal Reflection Method With Easy Calibration Using Two Stereo-Calibrated Video Cameras," in IEEE Transactions on Biomedical Engineering, vol. 60, No. 10, pp. 2952-2960, Oct. 2013. doi: 10.1109/TBME.2013.2266478.*
Extended European Search Report dated Jan. 24, 2018 for corresponding European Patent Application No. 17181824.8, 9 pages.

* cited by examiner

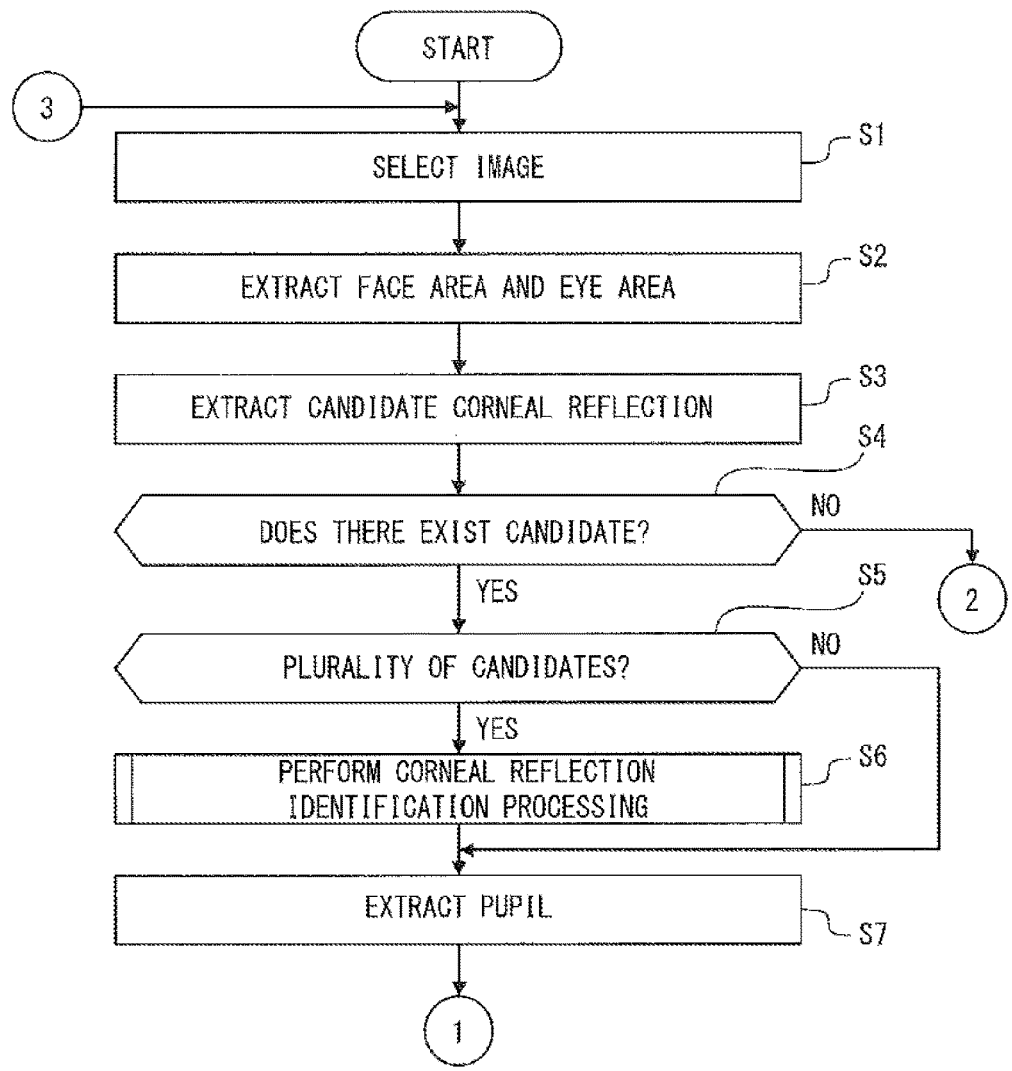
F I G. 4 A

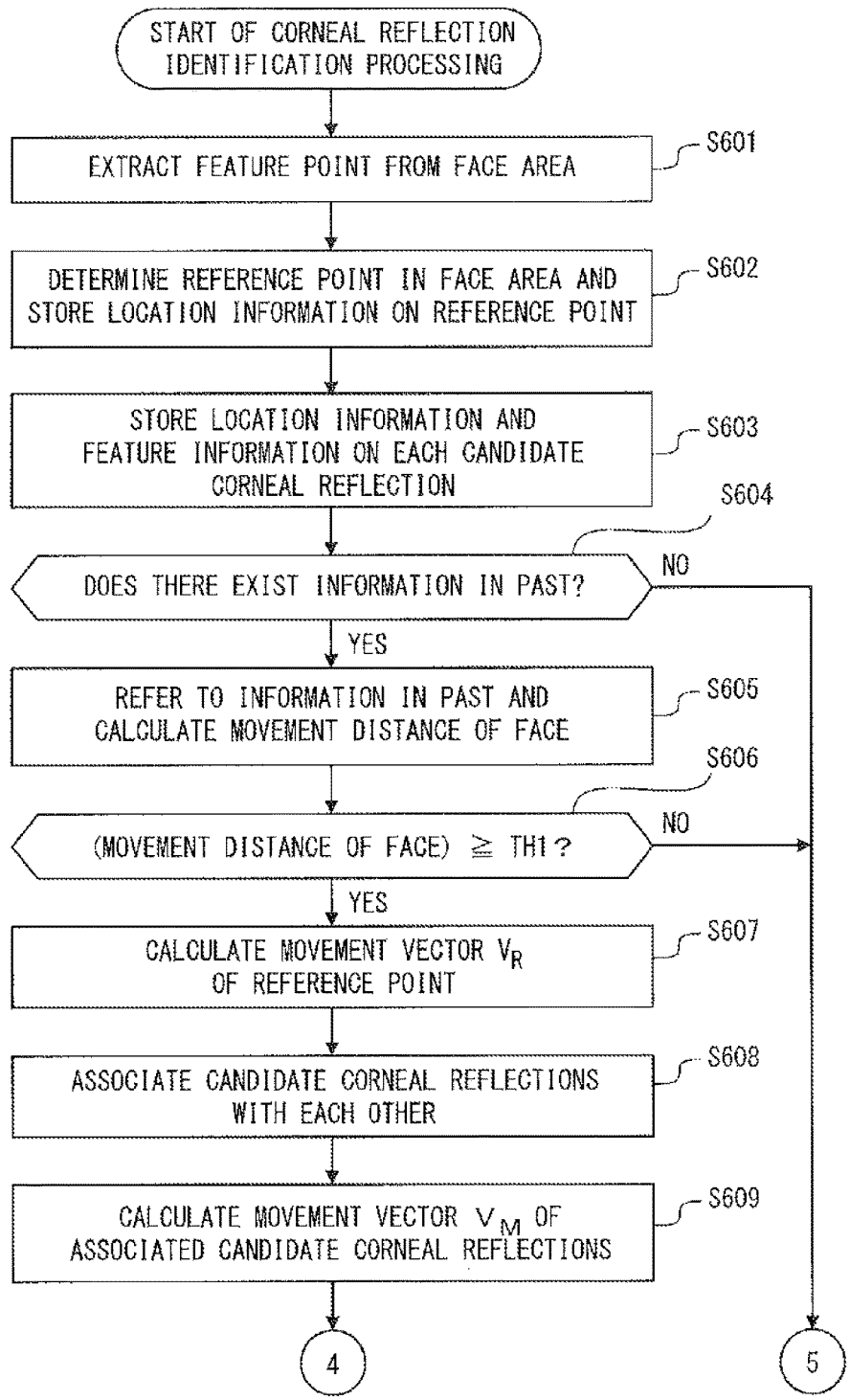
F I G. 5 A

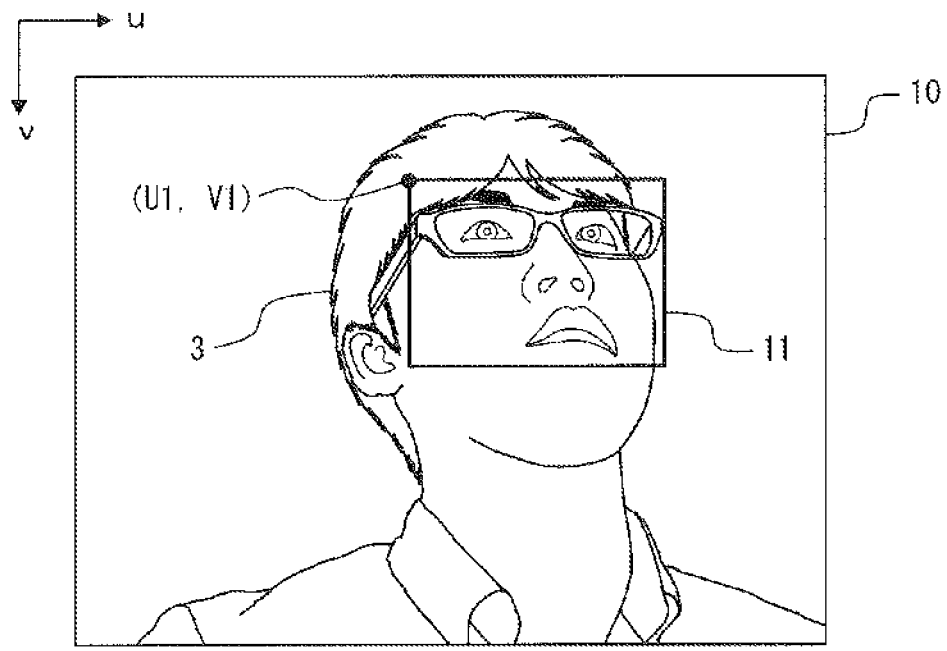
F I G. 6 A
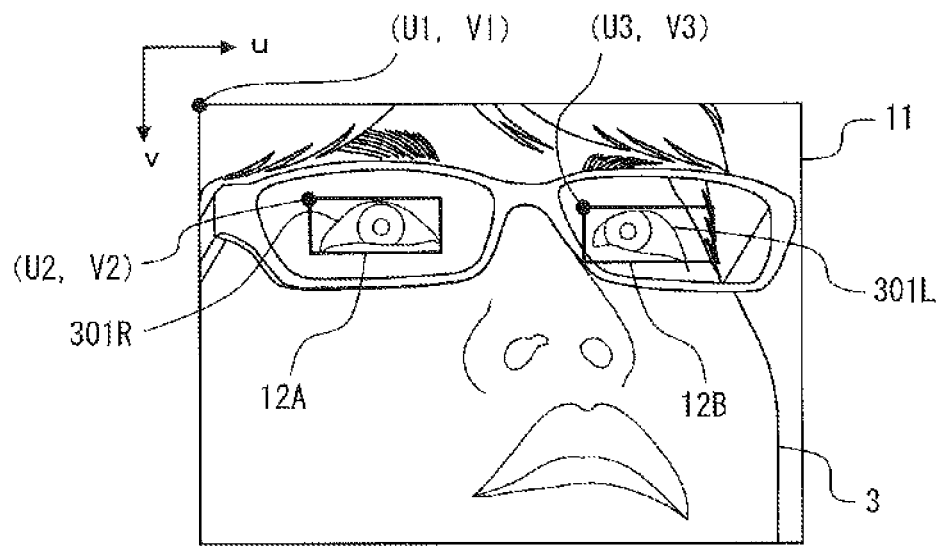
F I G. 6 B

LINE-OF-SIGHT DETECTION DEVICE AND LINE-OF-SIGHT DETECTION METHOD

CROSS-REFERENCE TO RELATED APPLICATION

This application is based upon and claims the benefit of priority of the prior Japanese Patent Application No. 2016-157681, filed on Aug. 10, 2016, the entire contents of which are incorporated herein by reference.

FIELD

The embodiments discussed herein are related to a line-of-sight detection device.

BACKGROUND

In recent years, line-of-sight detection technologies have been used in, for example, shops or digital signage as well as in a user interface of a personal computer to conduct research on a product or information that a customer has an interest in. For example, in a line-of-sight technology, an infrared image is captured that includes the head of a user onto which infrared light is radiated, so as to detect a line of sight of the user on the basis of a location of a corneal reflection and a location of a pupil in the infrared image.

In this type of line-of-sight detection technology, when a person whose line of sight is to be detected is wearing glasses, infrared light is reflected onto a lens of the glasses, and a reflection of infrared light that is different from a corneal reflection may be seen on a portion of the lens of the glasses in a captured image. This reflection of infrared light that is different from a corneal reflection may prevent an extraction of a corneal reflection.

As a method for preventing a reflection of infrared light onto a lens of glasses from appearing in an image, a method is known that includes arranging two sets of an infrared light source and an image-capturing device away from each other and changing the set to be used from one set to the other according to an orientation of the face of a person (see, for example, Document 1)

A method is known that distinguishes a corneal reflection from a reflection onto a lens of glasses by detecting, as a corneal reflection, a reflection that occurs intermittently using the fact that a corneal reflection does not appear in an image when the eyes are closed due to blinking (see, for example, Document 2).

Document 1: Japanese Laid-open Patent Publication No. 2006-167256

Document 2: Japanese Laid-open Patent Publication No. 2012-239550

SUMMARY

According to an aspect of the embodiment, a line-of-sight detection device includes a memory configured to store an image of a person that includes eyes of the person, and a processor configured to detect a line of sight of the person on the basis of the image stored in the memory, wherein the detecting the line of sight of the person includes extracting a candidate corneal reflection having a specified feature from a first image and from a second image captured after the first image is captured, extracting a reference point on the person from the first image and from the second image, calculating a threshold vector on the basis of a movement vector of the reference point and a predetermined threshold, wherein the movement vector has a start point at a location, in the second image, that overlaps the reference point in the first image and an end point at the reference point in the second image, and the threshold vector has a start point at a candidate location, in the second image, that overlaps a location of the candidate corneal reflection in the first image, calculating a movement vector of a reflection location that has a start point at the candidate location in the second image and an end point at a location of the candidate corneal reflection extracted from the second image, and identifying, on the basis of the threshold vector and the movement vector of the reflection location, a corneal reflection from among a plurality of candidate corneal reflections extracted from the second image so as to identify a location of the corneal reflection; extracting a location of a pupil from the image, and calculating the line of sight of the person in the image on the basis of the identified location of the corneal reflection and the extracted location of the pupil.

The object and advantages of the embodiment will be realized and attained by means of the elements and combinations particularly pointed out in the claims.

It is to be understood that both the foregoing general description and the following detailed description are exemplary and explanatory and are not restrictive of the embodiment.

BRIEF DESCRIPTION OF DRAWINGS

FIGS. 4A and 4B are a flowchart that illustrates processing performed by the line-of-sight detection device according to the embodiment;

FIGS. 5A and 5B are a flowchart that illustrates details of corneal reflection identification processing;

FIGS. 6A and 6B illustrate examples of a face area and an eye area;

DESCRIPTION OF EMBODIMENTS

Preferred embodiments of the present invention will be explained with reference to accompanying drawings.

In the case of a line-of-sight device in which two sets of an infrared light source and an image-capturing device are arranged away from each other and the set to be used is changed from one set to the other according to an orientation of the face of a person, installation costs are increased and the device is made larger.

Further, a time period in which the eyes are closed while blinking is very short. Thus, when an image-capturing interval is long (when a frame rate is low), or when the number of images is reduced and processing is performed on the reduced images, an image containing closed eyes occurs at long intervals, which may result in being unable to obtain or in taking a long time to obtain a sufficient amount of images containing a blink to perform processing. Thus, it is difficult to detect a corneal reflection correctly when a line of sight of a person who is wearing glasses is detected, which may result in being unable to detect a line of sight correctly. Embodiments for a device and a method for detecting a line of sight will be described below, the device and the method making it possible to accurately detect a line of sight of a person who is wearing glasses with a simple configuration.

Figure 1:
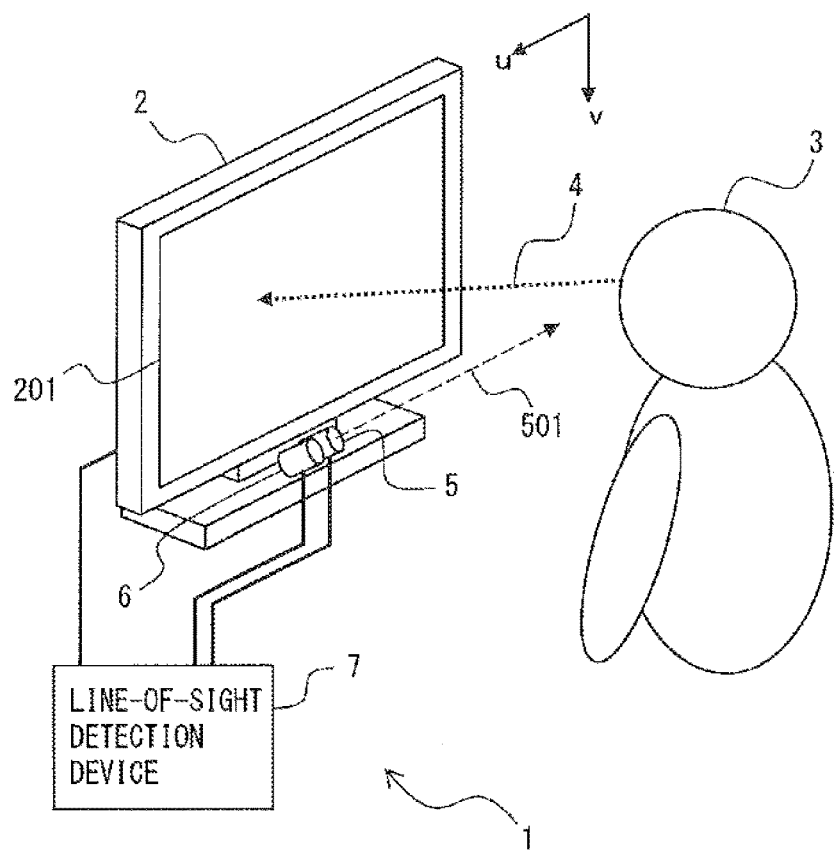
FIG. 1 illustrates an example of a configuration of a line-of-sight detection system.

FIG. 1 illustrates an example of a configuration of a line-of-sight detection system.

For example, as illustrated in FIG. 1, a line-of-sight detection system 1 is used to detect a line of sight 4 of a person 3 who is observing a display surface 201 of a display device 2. The line-of-sight detection system 1 includes an infrared light source 5, an image-capturing device 6, and a line-of-sight detection device 7. The infrared light source 5 is, for example, an infrared light emitting diode. The infrared light source 5 is arranged near the display device 2 so as to be directed to emit infrared light 501 toward the head of the person 3 who is observing the display surface 201 of the display device 2. The image-capturing device 6 is an infrared camera. The image-capturing device 6 is arranged near the display device 2 so as to be directed to capture an infrared image that includes the head of the person 3 who is observing the display surface 201 of the display device 2. The line-of-sight detection device 7 detects the line of sight 4 of the person 3 on the basis of a location of a corneal reflection and a location of a pupil in a portion of the eye (eyeball) of the person 3 in an infrared image captured by the image-capturing device 6. In other words, the line-of-sight detection device 7 detects the line of sight 4 of the person 3 by the pupil center corneal reflection technique. The line of sight 4 of the person 3 that is detected by the line-of-sight detection device 7 is used to, for example, input a line of sight on the basis of what a line of sight of the person 3 is directed towards on the display surface 201 of the display device 2 (that is, what the person 3 is looking at on the display surface 201).

Figure 2:
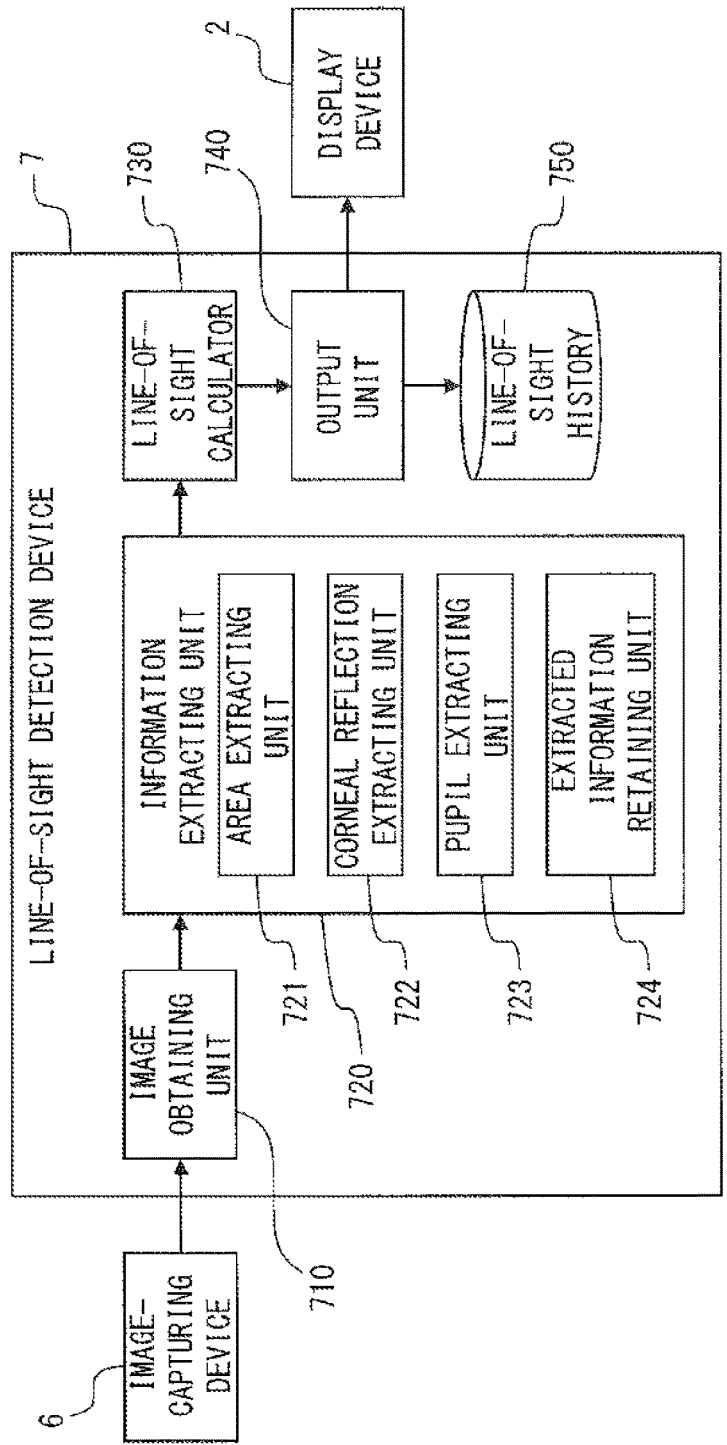
FIG. 2 illustrates a functional configuration of a line-of-sight detection device according to an embodiment.

FIG. 2 illustrates a functional configuration of a line-of-sight detection device according to an embodiment.

As illustrated in FIG. 2, the line-of-sight detection device 7 includes an image obtaining unit 710, an information extracting unit 720, a line-of-sight calculator 730, and an output unit 740. The line-of-sight detection device 7 further includes a storage (not illustrated) that stores a line-of-sight history 750.

The image obtaining unit 710 obtains an infrared image from the image-capturing device 6.

The information extracting unit 720 extracts information used to calculate a line of sight of the person 3 from a portion of the eye of the person 3 in the obtained infrared image, the information including a location of a corneal reflection and a location of a pupil. The information extracting unit 720 includes an area extracting unit 721, a corneal reflection extracting unit 722, a pupil extracting unit 723, and an extracted information retaining unit 724.

The line-of-sight calculator 730 calculates a line of sight of the person 3 on the basis of the location of a corneal reflection and the location of a pupil that are extracted by the information extracting unit 720. The line-of-sight calculator 730 calculates the line of sight of the person 3 according to a known calculation method in the pupil center corneal reflection technique.

The output unit 740 accumulates, in the line-of-sight history 750, the line of sight of the person 3 that is calculated by the line-of-sight calculator 730, and outputs it to an external device such as the display device 2.

As described above, the information extracting unit 720 included in the line-of-sight detection device 7 according to the present embodiment includes the area extracting unit 721, the corneal reflection extracting unit 722, the pupil extracting unit 723, and the extracted information retaining unit 724.

The area extracting unit 721 extracts a face area and an eye area of the person 3 from the obtained infrared image. The area extracting unit 721 extracts the face area and the eye area of the person 3 according to a known extracting method in the field of image analysis.

The corneal reflection extracting unit 722 extracts a corneal reflection that exists in the eye area extracted from the infrared image, and calculates a location of the extracted corneal reflection. The corneal reflection extracting unit 722 extracts the corneal reflection according to a known extracting method in the pupil center corneal reflection technique. When a plurality of candidate corneal reflections are extracted from one eye area, the corneal reflection extracting unit 722 according to the present embodiment identifies a corneal reflection from among the plurality of candidate corneal reflections. For example, the corneal reflection extracting unit 722 identifies a corneal reflection on the basis of a movement vector of a reference point and a movement vector of a candidate corneal reflection in face areas in two infrared images.

The pupil extracting unit 723 extracts a pupil that exists in the eye area extracted from the infrared image, and calculates a location of the extracted pupil. The pupil extracting unit 723 extracts the pupil according to a known extracting method in the pupil center corneal reflection technique.

The extracted information retaining unit 724 retains a face area, an eye area, a location of a candidate corneal reflection, and a location of a reference point in the face area that are extracted from each of a plurality of infrared images obtained by the image obtaining unit 710.

Figure 3:
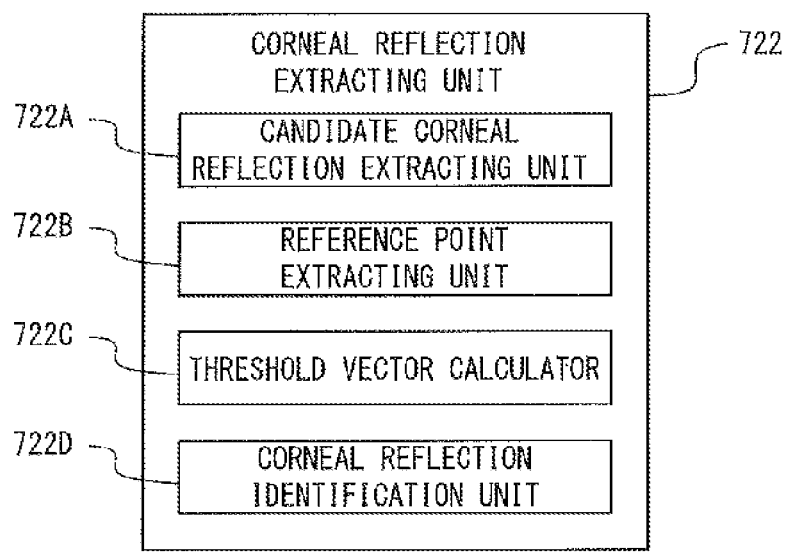
FIG. 3 illustrates a functional configuration of a corneal reflection extracting unit.

FIG. 3 illustrates a functional configuration of a corneal reflection extracting unit.

As illustrated in FIG. 3, the corneal reflection extracting unit 722 according to the present embodiment includes a candidate corneal reflection extracting unit 722A, a reference point extracting unit 722B, a threshold vector calculator 722C, and a corneal reflection identification unit 722D.

The candidate corneal reflection extracting unit 722A extracts a candidate corneal reflection according to a known extracting method in the pupil center corneal reflection technique. Here, the candidate corneal reflection is not limited to a corneal reflection, but includes a reflection that seems to be a corneal reflection in an eye area such as a reflection of infrared light onto a lens of glasses.

The reference point extracting unit 722B extracts, from the obtained image, a reference point on a person in the obtained image. The reference point may be, for example, a specified point on glasses worn by the person, or a feature in the face of the person such as an eyebrow.

The threshold vector calculator 722C calculates a threshold vector used when a corneal reflection is identified from among candidate corneal reflections. For example, first, the threshold vector calculator 722C calculates a movement vector of a reference point in a second image being captured after a first image is captured. A start point of the movement vector of the reference point is a location in the second image that overlaps the reference point in the first image. An end point of the movement vector of the reference point is a reference point in the second image. In other words, the threshold vector calculator 722C calculates a movement vector of a reference point that has a start point at a location, in a second image, that overlaps the reference point in a first image and an end point at the reference point in the second image, the second image being captured after the first image is captured. Further, on the basis of the calculated movement vector of the reference point and a predetermined threshold, the threshold vector calculator 722C calculates a threshold vector that has a start point at a location, in the second image, that overlaps a location of a candidate corneal reflection in the first image (hereinafter also referred to as a "candidate location").

The corneal reflection identification unit 722D identifies a corneal reflection from among a plurality of candidate corneal reflections extracted from the second image so as to identify a location of the corneal reflection. The corneal reflection identification unit 722D calculates a movement vector of a reflection location that has a start point at the candidate location in the second image and an end point at a location of the candidate corneal reflection that is extracted from the second image. Further, the corneal reflection identification unit 722D identifies a corneal reflection from a plurality of candidate corneal reflections extracted from the second image on the basis of the threshold vector and the movement vector of the reflection location so as to identify a location of the corneal reflection.

When the line-of-sight detection device 7 according to the present embodiment starts operating, the line-of-sight detection device 7 starts obtaining an infrared image captured by the image-capturing device 6 using the image obtaining unit 710. After that, the line-of-sight detection device 7 performs processing on each obtained infrared image, for example, according to the flowchart illustrated in FIGS. 4A and 4B. The infrared image captured by the image-capturing device 6 is hereinafter simply referred to as an "image".

Figure 4B:
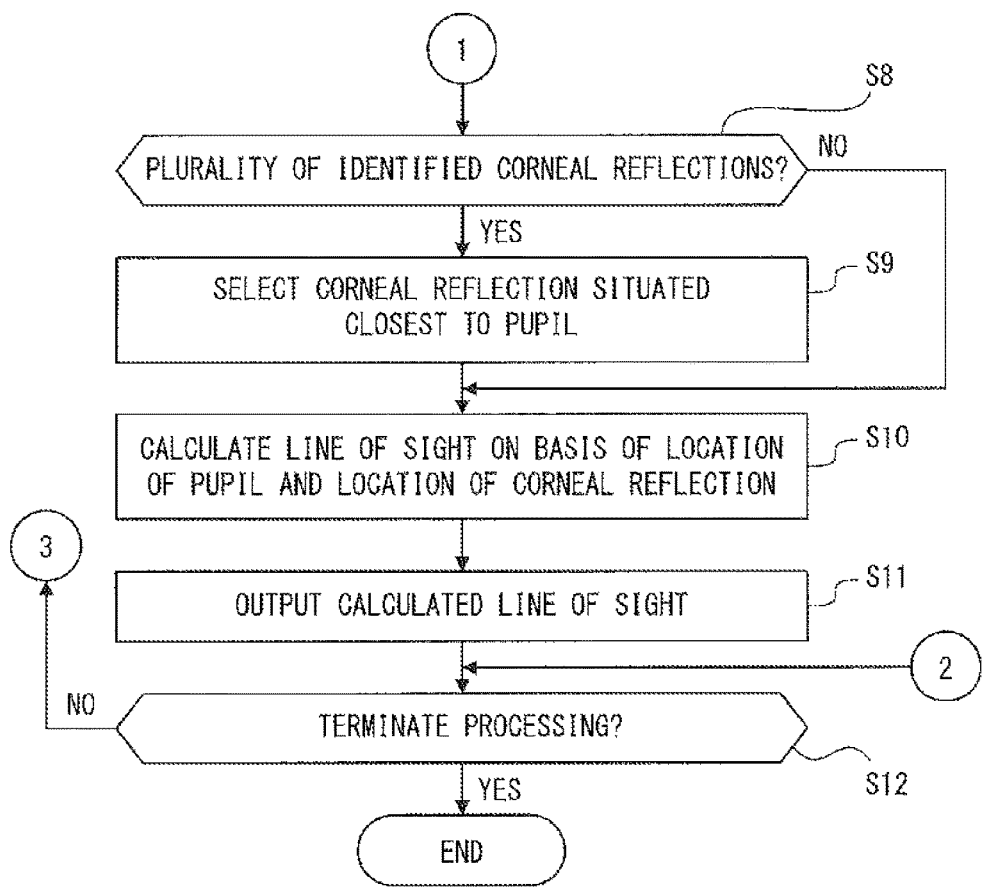

FIGS. 4A and 4B are a flowchart that illustrates processing performed by the line-of-sight detection device according to the embodiment.

First, the line-of-sight detection device 7 selects, from among obtained images, an image in which a line of sight is to be detected, as illustrated in FIG. 4A (Step S1). The process of Step S1 is performed by the image obtaining unit 710 or the information extracting unit 720. For example, the image obtaining unit 710 or the information extracting unit 720 selects, to be a target for a detection of a line of sight, one of the obtained images that has not been selected yet and was captured at an earliest time (an oldest image).

Next, the line-of-sight detection device 7 extracts a face area and an eye area from the selected image (Step S2). The process of Step S2 is performed by the area extracting unit 721 of the information extracting unit 720. The area extracting unit 721 extracts the face area and the eye area of the person 3 according to the known extracting method in the field of image analysis.

Next, the line-of-sight detection device 7 extracts a candidate corneal reflection included in the eye area extracted from the image (Step S3). The process of Step S3 is performed by the candidate corneal reflection extracting unit 722A included in the corneal reflection extracting unit 722 of the information extracting unit 720. The candidate corneal reflection extracting unit 722A extracts the candidate corneal reflection according to the known extracting method in the pupil center corneal reflection technique.

After Step S3, the corneal reflection extracting unit 722 determines whether there exists a candidate corneal reflection (Step S4). When there exists no candidate corneal reflection (Step S4; NO), the corneal reflection extracting unit 722 causes the line-of-sight detection device 7 to skip Steps S5 to S11 and to perform a determination in Step S12 as illustrated in FIG. 4B.

When there exists a candidate corneal reflection (Step S4; YES), the corneal reflection extracting unit 722 then determines whether there exist a plurality of candidate corneal reflections (Step S5). When there exist a plurality of extracted candidate corneal reflections (Step S5; YES), the corneal reflection extracting unit 722 performs corneal reflection identification processing that is processing of identifying a corneal reflection from among the plurality of candidate corneal reflections (Step S6). In Step S6, for example, the corneal reflection extracting unit 722 identifies a corneal reflection on the basis of a movement vector of a reference point and a movement vector of a candidate corneal reflection in face areas in two infrared images.

When the corneal reflection identification processing is completed, the corneal reflection extracting unit 722 causes the pupil extracting unit 723 to perform processing of extracting a pupil included in the eye area (Step S7). In the process of Step S7, the pupil extracting unit 723 extracts the pupil according to the known extracting method in the pupil center corneal reflection technique.

On the other hand, when the number of extracted candidate corneal reflections is one (Step S5; NO), the corneal reflection extracting unit 722 skips the corneal reflection identification processing of Step S6, and causes the pupil extracting unit 723 to perform the processing of extracting a pupil included in the eye area (Step S7).

When the process of Step S7 is completed, the line-of-sight detection device 7 determines whether there exist a plurality of identified corneal reflections as illustrated in FIG. 4B (Step S8). The determination of Step S8 is performed by, for example, the line-of-sight calculator 730. The line-of-sight calculator 730 determines whether there exist, in one eye area, a plurality of reflections identified as being a corneal reflection in Step S6. When there exist a plurality of identified corneal reflections (Step S8; YES), the line-of-sight calculator 730 selects a corneal reflection situated closest to the pupil among the plurality of corneal reflections (Step S9), and calculates a line of sight on the basis of a location of the pupil and a location of the corneal reflection (Step S10). On the other hand, when the number of identified corneal reflections is one (Step S8; NO), the line-of-sight calculator 730 skips the process of Step S9, and calculates the line of sight on the basis of the location of the pupil and the location the corneal reflection (Step S10). In the process of Step S10, the line-of-sight calculator 730 calculates a line of sight of the person 3 according to the known calculation method in the pupil center corneal reflection technique.

When the process of Step S10 is completed, the line-of-sight detection device 7 then outputs the calculated line of sight (Step S11). The process of Step S11 is performed by the output unit 740. The output unit 740 accumulates, in the line-of-sight history 750, information on a line of sight of the person 3 that is calculated by the line-of-sight calculator 730. In Step S11, for example, the output unit 740 may calculate a location of the line of sight on the display surface 201 of the display device 2 on the basis of the line of sight that is calculated by the line-of-sight calculator 730, and may output the location of the line of sight to the external device such as the display device 2.

After the line-of-sight detection device 7 outputs the calculated line of sight, the line-of-sight detection device 7 determines whether a series of processing (Steps S1 to S11) is to be terminated (Step S12). For example, when the person 3 situated within an image-capturing range of the image-capturing device 6 moves to the outside of the image-capturing range, or when the person 3 or another person performs a manipulation on the line-of-sight detection device 7 to make a request that a detection of a line of sight be terminated, the line-of-sight detection device 7 terminates the series of processing (Step S12; YES). On the other hand, when it has been determined that the series of processing is to be performed continually (Step S12; NO), the line-of-sight detection device 7 repeats the processes of Steps S1 to S11.

As described above, when there exist a plurality of candidate corneal reflections in one eye area extracted from one image, the corneal reflection extracting unit 722 of the line-of-sight detection device 7 according to the present embodiment performs the corneal reflection identification processing that is processing of identifying a corneal reflection from the plurality of candidate corneal reflections (Step S6). For example, the corneal reflection extracting unit 722 performs processing according to the flowchart illustrated in FIGS. 5A and 5B as the corneal reflection identification processing.

Figure 5B:
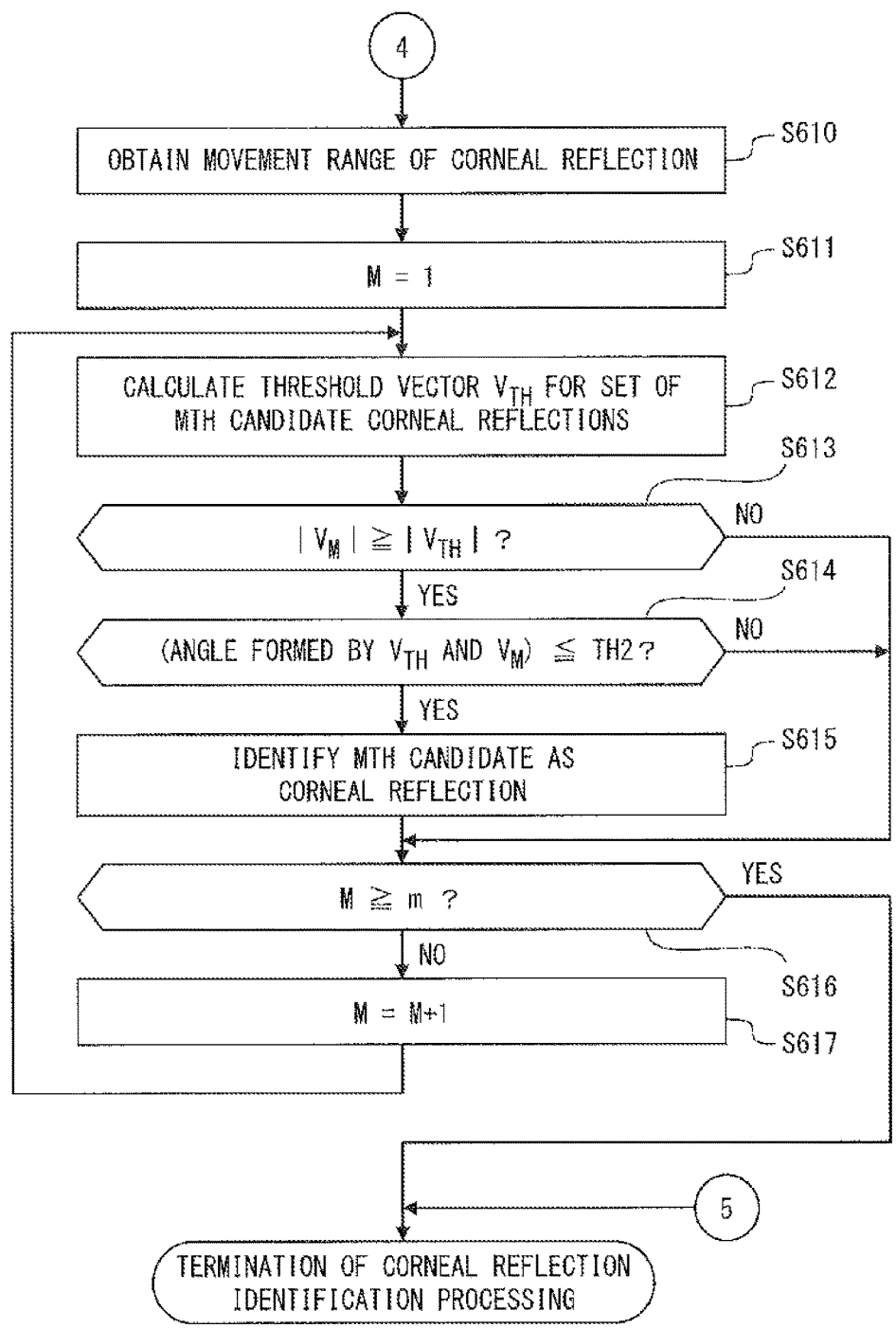

FIGS. 5A and 5B are a flowchart that illustrates details of the corneal reflection identification processing.

In the corneal reflection identification processing, first, the corneal reflection extracting unit 722 extracts a feature point from the face area, as illustrated in FIG. 5A (Step S601). The process of Step S601 is performed by, for example, the reference point extracting unit 722B. For example, the reference point extracting unit 722B performs, for example, edge detection processing on a face area extracted from an image, so as to extract a feature point in the face area.

Next, the corneal reflection extracting unit 722 determines a reference point in the face area on the basis of the extracted feature point and stores location information on the reference point (Step S602). The process of Step S602 is performed by the reference point extracting unit 722B. When the corneal reflection identification processing is performed (that is, when there exist a plurality of candidate corneal reflections in one eye area), the person 3 who appears in the image is more likely to be wearing glasses. Thus, using, for example, a connection point between a rim and a bridge in a frame of the glasses as a reference point, the reference point extracting unit 722B determines a location of the reference point in the face area. The reference point extracting unit 722B associates location information on the reference point with an identifier of the image to be processed, and stores (retains) the associated information in the extracted information retaining unit 724.

Next, the corneal reflection extracting unit 722 stores location information and feature information on each candidate corneal reflection (Step S603). The process of Step S603 is performed by, for example, the candidate corneal reflection extracting unit 722A. The candidate corneal reflection extracting unit 722A associates the location information and the feature information with an identifier of the image to be processed, and stores (retains) the associated pieces of information in the extracted information retaining unit 724, wherein, for example, the location information indicates a location of the center of the corneal reflection and the feature information indicates a size of the corneal reflection.

Next, the corneal reflection extracting unit 722 refers to the extracted information retaining unit 724 and determines whether there exists, for example, location information on the reference point that was stored when the corneal reflection identification processing was performed in the past (Step S604). The determination of Step S604 is performed by, for example, the threshold vector calculator 722C. Here, the corneal reflection identification processing performed in the past is assumed to be the corneal reflection identification processing which was performed from a point in time at which line-of-sight detection processing on a certain person 3 was started up to a point in time just before the current corneal reflection identification processing is performed. When there exists no information in the past (Step S604; NO), the corneal reflection extracting unit 722 skips the processes of Steps S605 to S617 and terminates the corneal reflection identification processing, as illustrated in FIGS. 5A and 5B. In this case, the corneal reflection extracting unit 722 identifies all of the plurality of candidate corneal reflections as a corneal reflection. Thus, after Steps S6 and S7, the line-of-sight calculator 730 determines that there exist a plurality of identified corneal reflections (Step S8; YES), and calculates a line of sight of the person 3 on the basis of a location of a corneal reflection situated closest to the pupil among the plurality of corneal reflections and a location of the pupil (Steps S9 and S10).

On the other hand, when there exists information in the past (Step S604; YES), the corneal reflection extracting unit 722 refers to the information in the past and calculates a movement distance of the face (Step S605). The process of Step S605 is performed by, for example, the threshold vector calculator 722C of the corneal reflection extracting unit 722. In Step S605, for example, the corneal reflection extracting unit 722 calculates a distance L (cm) from the image-capturing device 6 to the face of the person 3 first. The distance L is calculated on the basis of the number of pixels in the face width in an image, a horizontal resolution of the image-capturing device 6, a horizontal angle of view of the image-capturing device 6, and the average width of the human face (for example, 14.29 cm). Next, the corneal reflection extracting unit 722 calculates a horizontal image-capturing range H (cm) of the image-capturing device 6 using Formula (1) below.

$$H = 2 \cdot \tan(\phi/2) \cdot L \quad (1)$$

$\phi$ in Formula (1) is a horizontal angle of view of the image-capturing device 6.

After that, the corneal reflection extracting unit 722 calculates a movement distance D of a face (cm) using Formula (2) below.

$$D = (W \cdot H)/HR \quad (2)$$

In Formula (2), W is the number of pixels that represents a movement width of a face in an image, and HR is a horizontal resolution.

After the movement distance D of a face is calculated, the corneal reflection extracting unit 722 determines whether the calculated movement distance D of a face is not less than a threshold TH1 (Step S606). The determination of Step S606 is performed by, for example, the corneal reflection identification unit 722D. When the movement distance D of a face is less than the threshold TH1 (Step S606; NO), the corneal reflection extracting unit 722 skips the processes of Steps S605 to S617 and terminates the corneal reflection identification processing, as illustrated in FIGS. 5A and 5B. In this case, the corneal reflection extracting unit 722 identifies all of the plurality of candidate corneal reflections as a corneal reflection. Thus, after Steps S6 and S7, the line-of-sight calculator 730 determines that there exist a plurality of identified corneal reflections (Step S8; YES), and calculates a line of sight of the person 3 on the basis of a location of a corneal reflection situated closest to the pupil among the plurality of corneal reflections and a location of the pupil (Steps S9 and S10).

On the other hand, when the movement distance D of a face is not less than the threshold TH1 (Step S606; YES), the corneal reflection extracting unit 722 then calculates a movement vector $V_R$ of the reference point (Step S607). The process of Step S607 is performed by, for example, the threshold vector calculator 722C of the corneal reflection extracting unit 722. In Step S607, the corneal reflection extracting unit 722 calculates the movement vector $V_R$ on the basis of the location information on the reference point determined in Step S602 and the location information on the reference point which is included in the information in the past that is referred to in Step S605.

Next, the corneal reflection extracting unit 722 associates candidate corneal reflections with each other (Step S608). The process of Step S608 is performed by, for example, the threshold vector calculator 722C of the corneal reflection extracting unit 722. In Step S608, the corneal reflection extracting unit 722 associates candidate corneal reflections with each other on the basis of the location information and the feature information on a corneal reflection in an image that is to be processed at present and on the basis of the location information and the feature information on the corneal reflection that are included in the information in the past that is referred to in Step S605.

Next, the corneal reflection extracting unit 722 calculates a movement vector $V_M$ of the associated candidate corneal reflections (Step S609). The process of Step S609 is performed by, for example, the corneal reflection identification unit 722D of the corneal reflection extracting unit 722.

Next, the corneal reflection extracting unit 722 obtains a movement range of a corneal reflection as illustrated in FIG. 5B (Step S610). The process of Step S610 is performed by, for example, the threshold vector calculator 722C of the corneal reflection extracting unit 722. The movement range of a corneal reflection is, for example, a maximum value of a movement range of an eyeball in a range in which a line of sight can be detected. For example, the line-of-sight detection device 7 stores, in the extracted information retaining unit 724 or the like and as a movement range of a corneal reflection, an amount of a movement of an eyeball when the person 3 gazes at an edge of the display surface 201 of the display device 2 upon perform calibration when processing of detecting a line of sight of the person 3 is started.

Next, the corneal reflection extracting unit 722 sets, to one, a variable M that identifies a set of candidate corneal reflections (Step S611). The process of Step S611 is performed by the threshold vector calculator 722C of the corneal reflection extracting unit 722.

Next, the corneal reflection extracting unit 722 calculates a threshold vector $V_{TH}$ for a set of Mth candidate corneal reflections (Step S612). The process of Step S612 is performed by the threshold vector calculator 722C of the corneal reflection extracting unit 722. In Step S612, the threshold vector calculator 722C calculates the threshold vector $V_{TH}$ using Formula (3) below.

$$V_{TH}=V_M-R\cdot(V_M/|V_M|) \quad (3)$$

R in Formula (3) is a radius of a circle that represents the movement range of a corneal reflection that is obtained in Step S610.

Next, the corneal reflection extracting unit 722 determines whether the size of the movement vector $V_M$ is not less than the size of the threshold vector $V_{TH}$ (Step S613). The determination of Step S613 is performed by the corneal reflection identification unit 722D of the corneal reflection extracting unit 722. When $|V_M| \geq |V_{TH}|$ (Step S613; YES), the corneal reflection identification unit 722D then determines whether an angle formed by the threshold vector $V_{TH}$ and the movement vector $V_M$ is not greater than a threshold TH2 (Step S614). When the angle formed by the threshold vector $V_{TH}$ and the movement vector $V_M$ is not greater than the threshold TH2 (Step S614; YES), the corneal reflection identification unit 722D identifies the Mth candidate corneal reflection as a corneal reflection (Step S615).

After that, the corneal reflection identification unit 722D determines whether the variable M is not less than a total number m of sets of candidate corneal reflections (Step S616). When $|V_M| < |V_{TH}|$ (Step S613; NO), the corneal reflection identification unit 722D skips Steps S614 and S615 and performs the determination of Step S616. When the angle formed by the threshold vector $V_{TH}$ and the movement vector $V_M$ is greater than the threshold TH2 (Step S614; NO), the corneal reflection identification unit 722D skips Step S615 and performs the determination of Step S616.

When M<m (Step S616; NO), the corneal reflection identification unit 722D updates the variable M to M=M+1 (Step S617), and repeats the processes of and after Step S612 in cooperation with the threshold vector calculator 722C. When M≥m (Step S616; YES), the corneal reflection identification unit 722D terminates the corneal reflection identification processing.

Figure 7:
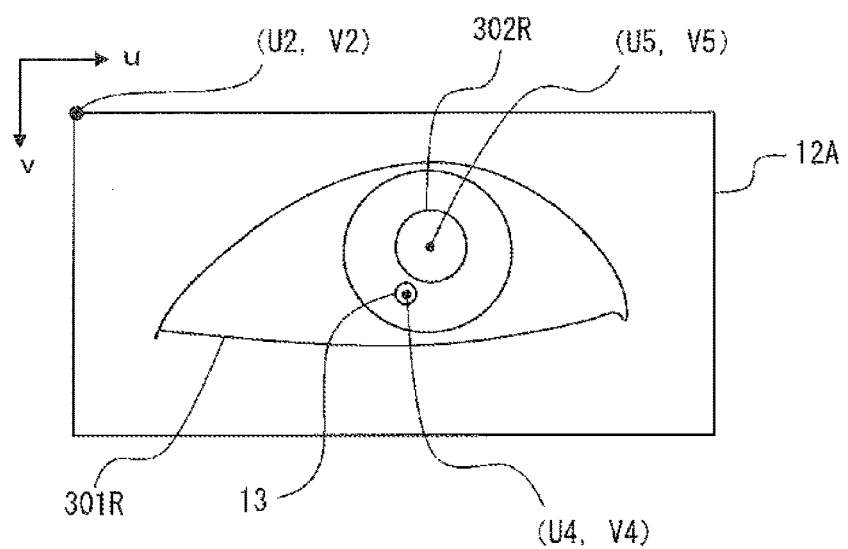
FIG. 7 illustrates an example of a corneal reflection in the eye area.

FIGS. 6A and 6B illustrate examples of a face area and an eye area. FIG. 7 illustrates an example of a corneal reflection in the eye area.

The line-of-sight detection device 7 according to the present embodiment obtains, for example, an image 10 illustrated in FIG. 6A, and extracts a face area 11 for the person 3 in the image 10 using the area extracting unit 721. For example, the face area 11 is a rectangular area and is specified by a coordinate of an upper left corner (U1,V1), the number of pixels in a horizontal direction (u direction), and the number of pixels in a vertical direction (v direction).

Further, the area extracting unit 721 extracts eye areas 12A and 12B that exist in the face area 11, as illustrated in FIG. 6B. The eye area 12A is a rectangular area that includes a right eye 301R of the person 3, and is specified by, for example, a coordinate of an upper left corner (U2,V2), the number of pixels in the horizontal direction (u direction), and the number of pixels in the vertical direction (v direction). The eye area 12B is a rectangular area that includes a left eye 301L of the person 3, and is specified by, for example, a coordinate of an upper left corner (U3,V3), the number of pixels in the horizontal direction (u direction), and the number of pixels in the vertical direction (v direction).

Here, with respect to one eye area 12A, there exists a corneal reflection 13 in a cornea of the right eye 301R, that is, a reflection of infrared light 501 emitted by the infrared light source 5, as illustrated in FIG. 7. The line-of-sight detection device 7 calculates a line of sight of the person who appears in the image on the basis of a location (U4,V4) of the corneal reflection 13 and a location (U5,V5) of a pupil 302R in the eye area 12A.

Here, when the person 3 who appears in the image is not wearing glasses, the number of reflections of the infrared light 501 in one eye area 12A is one, and it is possible to identify the reflection as the corneal reflection 13. However, when the person 3 who appears in the image is wearing glasses, the infrared light 501 is reflected not only onto the cornea of the eye, but also onto a lens of the glasses. Thus, when the person 3 who appears in the image is wearing glasses, there exist a plurality of reflections of the infrared light 501 in one eye area, which results in it being difficult to identify a corneal reflection. Thus, in the present embodiment, when there exist a plurality of reflections of the infrared light 501 in one eye area, the corneal reflection identification processing (Step S6) is performed so as to identify a corneal reflection from among the plurality of reflections (a plurality of candidate corneal reflections). In the corneal reflection identification processing, a corneal reflection is identified from among a plurality of candidate corneal reflections using a movement of the face of a person in an image, as described above.

Figure 8:
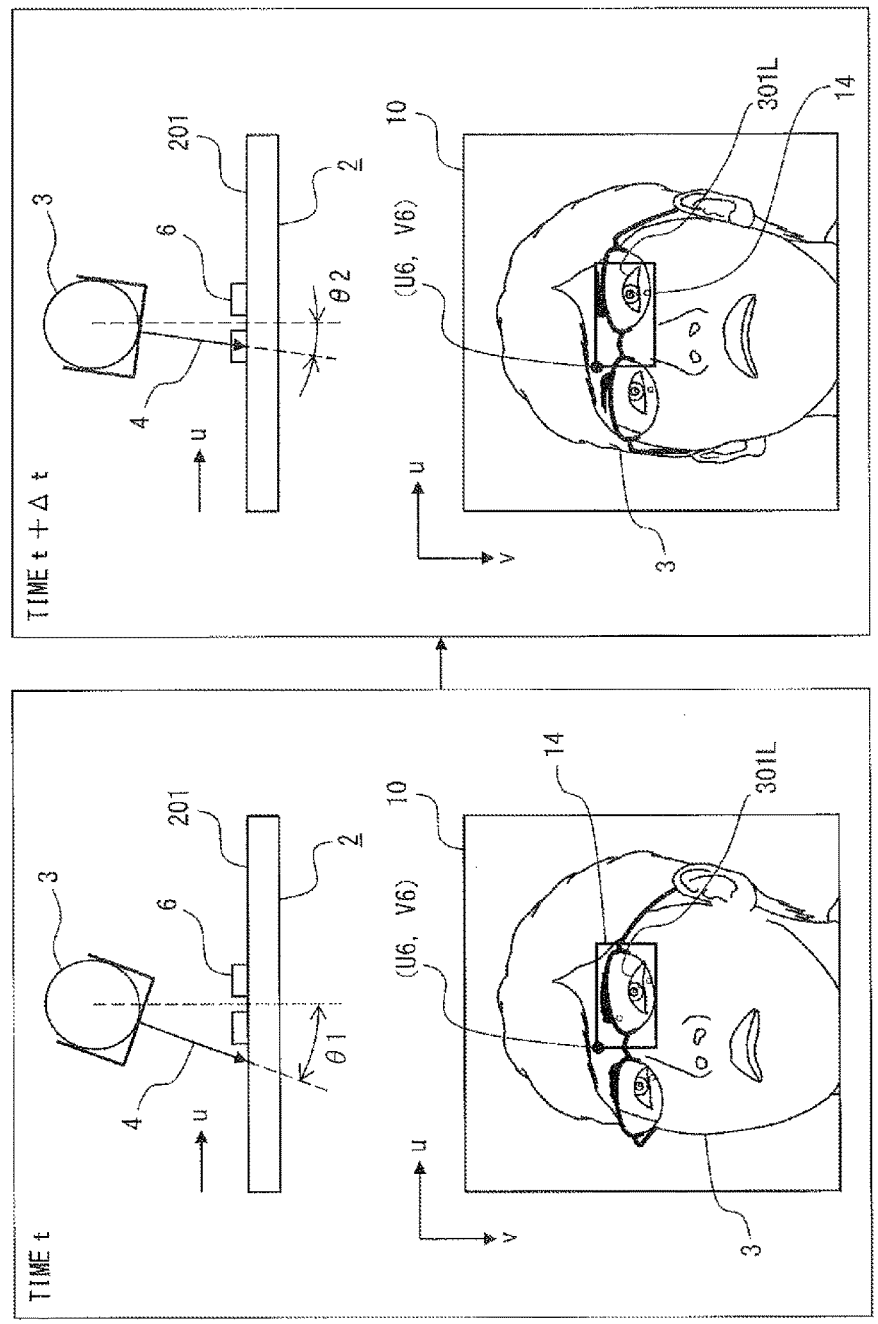
FIG. 8 illustrates examples of a movement of a face.

FIG. 8 illustrates examples of a movement of a face.

FIG. 8 illustrates examples of an orientation of the face of the person 3 and the image 10 captured by the image-capturing device 6 at a time t and a time t+Δt. The line of sight 4 of the person 3 at the time t shifts clockwise (leftward) by an angle θ1 from a line of sight in a face direction of the display surface 201 of the display device 2. The line of sight 4 of the person 3 at the time t+Δt shifts clockwise by an angle θ2 (<θ1) from the line of sight in the face direction of the display surface 201 of the display device 2. Here, a time difference Δt is, for example, about 0.1 to 0.3 seconds.

The image-capturing device 6 is arranged near the display device 2 and its image-capturing range is unchanged. Thus, when the person 3 who is observing the display surface 201 of the display device 2 changes the direction of the face to change the direction of the line of sight 4, the direction of the face of the person 3 in the image 10 is changed accordingly. Thus, in a comparison between the image 10 at the time t and the image 10 at the time t+Δt with respect to a rectangular area 14 that has an upper left corner at a location (U6,V6), the location of the left eye 301L in the rectangular area 14 moves.

Figure 9:
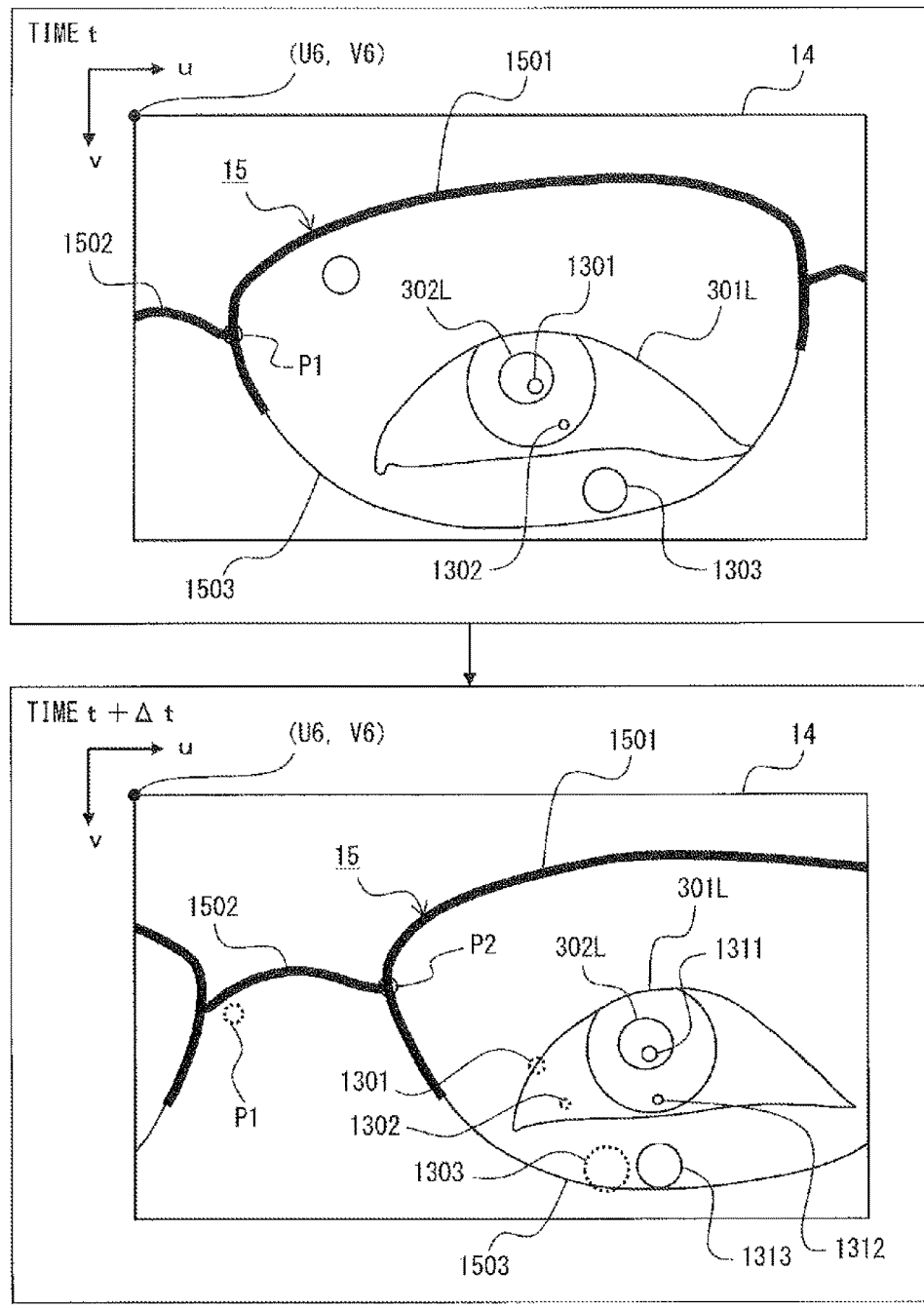
FIG. 9 illustrates examples of a corneal reflection and a glasses reflection.

FIG. 9 illustrates examples of a corneal reflection and a glasses reflection. FIG. 9 illustrates the rectangular area 14 in the image 10 at the time t and the rectangular area 14 in the image 10 at the time t+Δt in FIG. 8.

The left eye 301L of the person 3 and a portion of glasses 15 appear in the rectangular area 14 in the image at the time t. Further, reflections 1301, 1302, and 1303 of infrared light emitted by the infrared light source 5 appear in the rectangular area 14 in the image at the time t. The reflection 1301 situated closest to the center of a pupil 302L of the left eye 301L among the three reflections 1301, 1302, and 1303 is a reflection of infrared light in the left eye 301L (corneal). The other two reflections 1302 and 1303 from among the three reflections 1301, 1302, and 1303 are reflections of infrared light in a lens 1503 for a left eye in the glasses 15 (glasses reflections).

Likewise, the left eye 301L of the person 3 and a portion of the glasses 15 appear in the rectangular area 14 in the image at the time t+Δt. Further, reflections 1311, 1312, and 1313 of infrared light emitted by the infrared light source 5 appear in the rectangular area 14 in the image at the time t+Δt. The reflection 1311 situated closest to the center of the pupil 302L of the left eye 301L among the three reflections 1311, 1312, and 1313 is a reflection of infrared light in a left eye 301L (corneal). The other two reflections 1312 and 1313 from among the three reflections 1311, 1312, and 1313 are reflections of infrared light in the lens 1503 for a left eye in the glasses 15 (glasses reflections).

As described above, when a person who appears in an image is wearing the glasses 15, the image includes a reflection of infrared light onto an eye (cornea) and a reflection of infrared light onto the lens 1503 of the glasses 15. In addition, it is difficult to distinguish the reflection of infrared light onto a cornea from the reflection of infrared light onto the lens 1503 by use of one image. Thus, in the present embodiment, a corneal reflection is identified from among a plurality of candidate corneal reflections on the basis of a movement vector of a reference point between the image 10 at the time t and the image 10 at the time t+Δt.

It is assumed that the reference point in the image 10 is a point that varies according to an orientation of a face and is, for example, a connection point P1,P2 of a rim 1501 and a bridge 1502 in the glasses 15. The reference point P1 represented by a dotted circle in the rectangular area 14 in the image at the time t+Δt in FIG. 9 indicates a location of a connection point of the rim 1501 and the bridge 1502 in the image (rectangular area 14) at the time t. On the other hand, the reference point P2 represented by a solid circle in the rectangular area 14 in the image at the time t+Δt in FIG. 9 indicates a location of a connection point of the rim 1501 and the bridge 1502 in the image (rectangular area 14) at the time t+Δt. Further, locations of the candidate corneal reflections 1301, 1302, and 1303 in the image (rectangular area 14) at the time t are each represented by a dotted circle in the rectangular area 14 in the image at the time t+Δt.

When the person 3 changes the direction of the face without moving the eyes, the movement direction and the movement amount of a corneal reflection is substantially the same as the movement direction and the movement amount of a reference point. On the other hand, the movement direction and the movement amount of a reflection onto the lens 1503 of the glasses 15 are significantly different from the movement direction and the movement amount of the reference point. In the corneal reflection identification processing according to the present embodiment, a corneal reflection is identified on the basis of a difference between the movement direction and the movement amount of a corneal reflection and the movement direction and the movement amount of a reflection onto the lens 1503 of the glasses 15, the difference occurring when the direction of the face is changed as described above. For example, compared with the direction and the amount of a movement from the reflection 1302 to the reflection 1312, the direction and the amount of a movement from the reflection 1301 to the reflection 1311 in the rectangular area 14 (the image) at the time t+Δt in FIG. 9 has a greater similarity to the direction and the amount of a movement from the reference point P1 to the reference point P2. Thus, it is possible to correctly extract a corneal reflection in a person who is wearing glasses by distinguishing the reflection 1311 from the reflections 1312 and 1313 using a threshold.

Figure 10A:
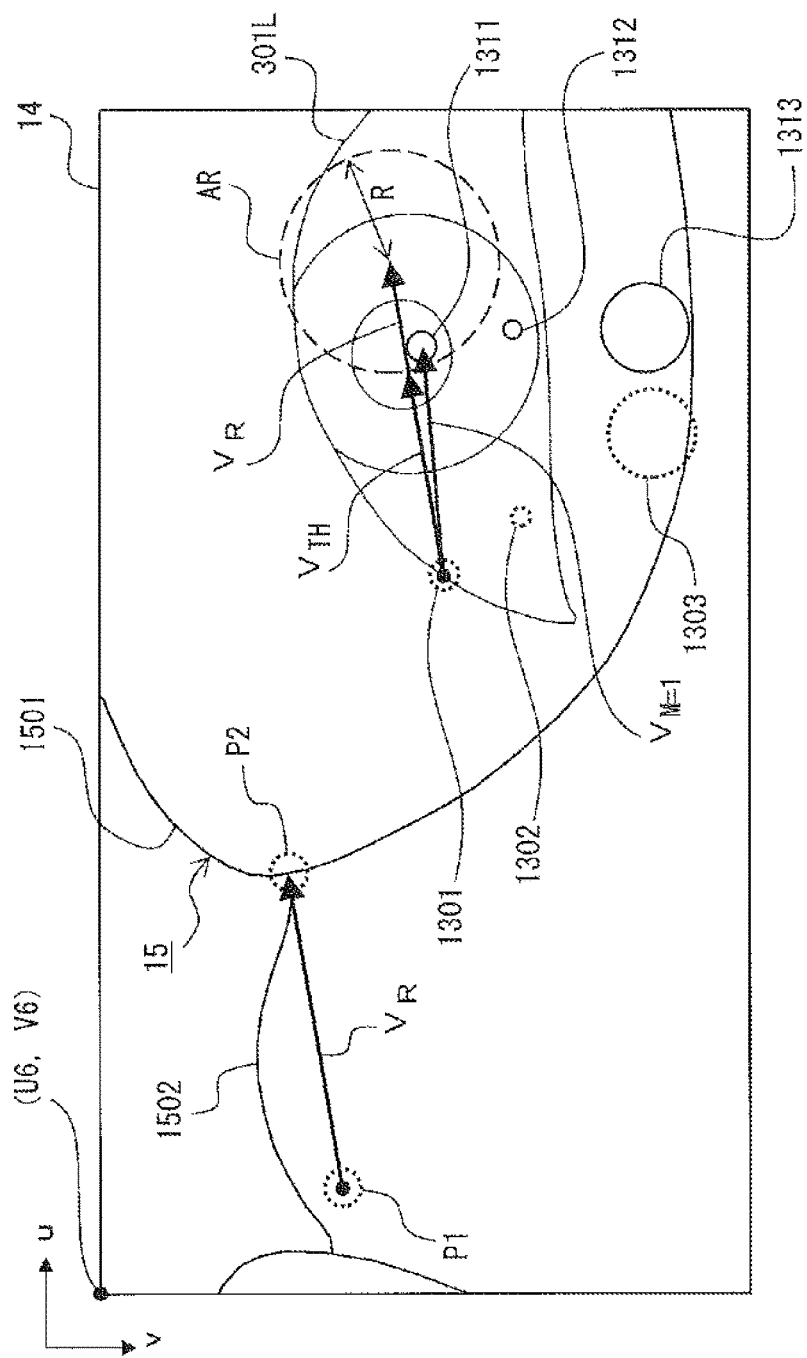
FIGS. 10A and 10B are diagrams that describe a method for identifying a corneal reflection.
Figure 10B:
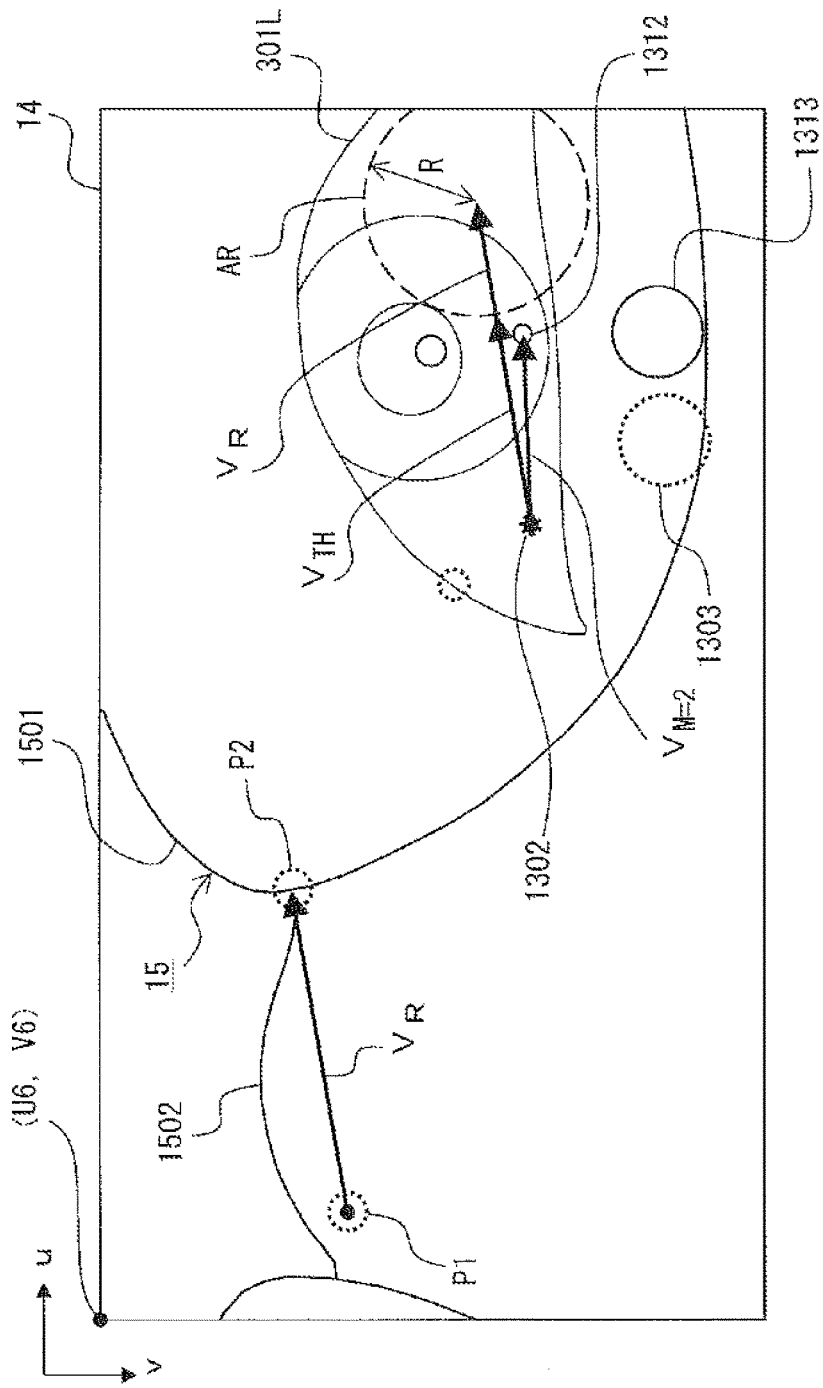

FIGS. 10A and 10B are diagrams that describe a method for identifying a corneal reflection. FIGS. 10A and 10B each illustrate the rectangular area 14 in the image 10 at the time t+Δt in FIG. 8. In the following descriptions with reference to FIGS. 10A and 10B, the rectangular area 14 is also referred to as an image at the time t+Δt.

In the corneal reflection identification processing according to the present embodiment (Step S6), when a corneal reflection in an image to be processed is identified, location information on a reference point that has been determined in the corneal reflection identification processing in the past is referred to, and a movement vector $V_R$ of the reference point is calculated (Step S607). Here, when the image to be processed is the image 10 at the time t+Δt in FIG. 8, the corneal reflection extracting unit 722 calculates, in Step S607, a movement vector $V_R$ of a reference point between the image 10 at the time t+Δt and, for example, the image 10 at the time t in FIG. 8. In this case, the movement vector $V_R$ of a reference point is a vector that has a start point at a location of the reference point P1 in the image at the time t+Δt (rectangular area 14) and an endpoint at the reference point P2 (that is, a vector directed from the reference P1 to the reference P2), as illustrated in FIG. 10A.

Next, the corneal reflection extracting unit 722 associates candidate corneal reflections with each other (Step S608). In Step S608, the corneal reflection extracting unit 722 associates candidate corneal reflections with each other on the basis of location information and feature information on each candidate corneal reflection that have been stored in the extracted information retaining unit 724. For example, the three reflections 1311, 1312, and 1313 in the image at the time t+Δt (rectangular area 14) illustrated in FIG. 10A are aligned in a substantially vertical direction (v direction), and the reflection 1313 situated in the lowest location is large. Further, the three reflections 1301, 1302, and 1303 in the image at the time t that are represented by dotted circles in FIG. 10A are aligned in a substantially vertical direction (v direction), and the reflection 1303 situated in the lowest location is large. Thus, the reflection 1311 situated in the highest location in the image at the time t+Δt is associated with the reflection 1301 situated in the highest location in the image at the time t. Further, the reflection 1313 situated in the lowest location in the image at the time t+Δt illustrated in FIG. 10A is associated with the reflection 1303 situated in the lowest location in the image at the time t. Furthermore, the reflection 1312 in the image at the time t+Δt illustrated in FIG. 10A is associated with the reflection 1302 in the image at the time t.

Next, the corneal reflection extracting unit 722 calculates a movement vector $V_M$ of the associated candidate corneal reflections (Step S609). In Step S609, first, the corneal reflection extracting unit 722 calculates a movement vector $V_{M=1}$ that is directed from the reflection 1301 situated in the highest location in the image at the time t to the reflection 1311 situated in the highest location in the image at the time t+Δt. Next, the corneal reflection extracting unit 722 calculates a movement vector $V_{M=2}$ (not illustrated) that is directed from the reflection 1302 in the image at the time t to the reflection 1312 in the image at the time t+Δt. Then, the corneal reflection extracting unit 722 calculates a movement vector $V_{M=3}$ (not illustrated) that is directed from the reflection 1303 in the image at the time t to the reflection 1313 in the image at the time t+Δt.

After that, the corneal reflection extracting unit 722 obtains a movement range of a corneal reflection (Step S610) and calculates a threshold vector $V_{TH}$ for a set of candidate corneal reflections in which M=1 (Step S612). In Step S610, the corneal reflection extracting unit 722 sets a movement vector $V_R$ of the reference point that has a start point at the location of the reflection 1301 in the image at the time t in the set of candidate corneal reflections in which M=1, as illustrated in FIG. 10A. Next, the corneal reflection extracting unit 722 sets, to be a movement range of a corneal reflection, an area AR of a radius R, whose center is the end point of the movement vector $V_R$. After that, the corneal reflection extracting unit 722 sets, to be the threshold vector $V_{TH}$ for the set of candidate corneal reflections in which M=1, a vector that is a shortest distance from the reflection 1301 to a point on the circumference of the area AR.

After the threshold vector $V_{TH}$ for the set of candidate corneal reflections in which M=1 is calculated, the corneal reflection extracting unit 722 determines whether $|V_{M=1}| \geq |V_{TH}|$ (Step S613). In the example illustrated in FIG. 10A, $|V_{M=1}| \geq |V_{TH}|$ (Step S613; YES). Thus, the corneal reflection extracting unit 722 then determines whether an angle formed by the threshold vector $V_{TH}$ and the movement vector $V_{M=1}$ is not greater than the threshold TH2 (Step S614). When the angle formed by the threshold vector $V_{TH}$ and the movement vector $V_{M=1}$ is not greater than the threshold TH2, the corneal reflection extracting unit 722 identifies, as a corneal reflection, the candidate corneal reflection 1311 in the image at the time t+Δt (rectangular area 14) in the set of candidate corneal reflections in which M=1 (Step S615).

When the processes of Steps S612 to S615 for the set of candidate corneal reflections in which M=1 are completed, the corneal reflection extracting unit 722 performs the processes of Steps S612 and S613 for a set of candidate corneal reflections in which M=2. Here, the corneal reflection extracting unit 722 sets an area AR of a radius R (a movement range of a corneal reflection) on the basis of a movement vector $V_R$ of the reference point that has a start point at the location of the reflection 1302 in the image at the time t (rectangular area 14), and calculates a threshold vector $V_{TH}$, as illustrated in FIG. 10B (Step S612). After that, the corneal reflection extracting unit 722 determines whether $|V_{M=2}| \geq |V_{TH}|$ (Step S613). In the example illustrated in FIG. 10B, $|V_{M=2}| < |V_{TH}|$ (Step S613; NO). Thus, the corneal reflection extracting unit 722 skips Steps S614 and S615 for the set of candidate corneal reflections in which M=2, and then performs the processes of Steps S612 and S613 for a set of candidate corneal reflections in which M=3. $|V_{M=3}| < |V_{TH}|$ in the set of candidate corneal reflections in which M=3 (Step S613; NO), although this is not illustrated. Thus, the corneal reflection extracting unit 722 skips Steps S614 and S615 for the set of candidate corneal reflections in which M=3, and performs the determination of Step S616. In the examples illustrated in FIGS. 10A and 10B, there are three sets of candidate corneal reflections (m=3). Thus, after it skips Steps S614 and S615 for the set of candidate corneal reflections in which M=3, the corneal reflection extracting unit 722 determines NO in Step S616 and terminates the corneal reflection identification processing.

The corneal reflection of the left eye 301L in the image 10 at the time t+Δt illustrated in FIG. 8 is identified by the processing described above.

As described above, the line-of-sight detection device 7 according to the present embodiment identifies a corneal reflection on the basis of a movement vector of a reference point that moves together with a person in an image, a movement vector of locations of a plurality of candidate corneal reflections extracted from one eye area in the image, and a threshold with respect to a movement range of a corneal reflection. In this case, with respect to a set of candidate corneal reflections in a first image and in a second image, the line-of-sight detection device 7 sets a threshold vector for the set of candidate corneal reflections on the basis of a movement vector of the reference point that has a start point at a location of the candidate corneal reflection in the first image and on the basis of the threshold with respect to the movement range of a corneal reflection. Then, when the size of the movement vector in the set of candidate corneal reflections is greater than the size of the threshold vector and when an angle formed by the movement vector and the threshold vector is not greater than an angle threshold TH2, the line-of-sight detection device 7 identifies the candidate corneal reflection as a corneal reflection. Thus, even when a person who appears in an image is wearing glasses, it is possible to identify a corneal reflection by excluding a reflection of infrared light onto a lens of the glasses.

It is also possible to identify a corneal reflection more accurately by selecting a set of the first image and the second image in which a movement vector of a reference point is greater than a threshold vector.

According to the present embodiment, even when a person who appears in an image has his/her eyes closed and only a reflection of infrared light onto a lens of glasses is extracted as a candidate corneal reflection, it is possible to identify a corneal reflection by excluding the reflection of infrared light onto the lens of the glasses.

Further, even when an image-capturing interval is long (even when a frame rate is low), or even when an image of a person with closed eyes does not occur regularly such as when the number of obtained images is reduced and processing is performed on the reduced obtained images, it is possible to identify a corneal reflection by excluding a reflection of infrared light onto a lens of glasses.

Furthermore, when the line-of-sight detection device 7 according to the present embodiment is used, it is possible to identify a corneal reflection by excluding a reflection of infrared light onto a lens of glasses by use of a set of the infrared light source 5 and the image-capturing device 6. Thus, it is possible to identify a corneal reflection accurately with a simple configuration, which results in being able to reduce the costs of a line-of-sight detection system.

In the present embodiment, a location of a corneal reflection in a second image (image at the time t+Δt) that is captured after a first image (image at the time t) is captured is identified on the basis of the first image and the second image. However, the corneal reflection identification processing according to the present embodiment is not limited to this, but a location of the corneal reflection in the first image may be identified on the basis of the first image and the second image.

Further, the reference point is not limited to the connection point of the rim 1501 and the bridge 1502 in the glasses 15 described above, but it is sufficient if the reference point is a point that moves together with an orientation of a face. For example, when a time interval (frame rate) upon capturing an image with the image-capturing device 6 is not less than tens of fps and the image-capturing speed is sufficiently faster than a movement of mimetic muscles, an eyebrow may be used as a reference point.

The flowchart illustrated in FIGS. 5A and 5B is just an example of the corneal reflection identification processing performed by the line-of-sight detection device 7 according to the present embodiment. The corneal reflection identification processing is not limited to being performed according to the procedure described above, but modifications can be made thereto as needed without departing from the spirit of the present embodiment.

The flowchart illustrated in FIGS. 4A and 4B is just an example of the processing performed by the line-of-sight detection device 7 according to the present embodiment. The processing performed by the line-of-sight detection device 7 according to the present embodiment is not limited to being performed according to the procedure described above, but modifications can be made thereto as needed without departing from the spirit of the present embodiment.

Further, the functional configuration of the line-of-sight detection device 7 according to the present embodiment is not limited to the configuration illustrated in FIG. 2, but modifications can be made thereto as needed without departing from the spirit of the present embodiment.

In addition, the line-of-sight detection device 7 according to the present embodiment is applicable not only to the line-of-sight detection system 1 having the configuration illustrated in FIG. 1, but also to various line-of-sight detection systems. For example, the line-of-sight detection device 7 is applicable to a line-of-sight detection system that detects a line of sight of a customer for the purpose of conducting research on which product the customer was interested in a shop. Further, for example, when the line-of-sight detection system 1 is a system that collects a result of detecting a line of sight of a person and when the result of detecting a line of sight is analyzed by a different external device, the display device 2 can be omitted.

The line-of-sight detection device 7 that performs the processing described above can be implemented using, for example, a computer and a program that is executed by the computer. The line-of-sight detection device 7 implemented using a computer and a program is described with reference to FIG. 11.

Figure 11:
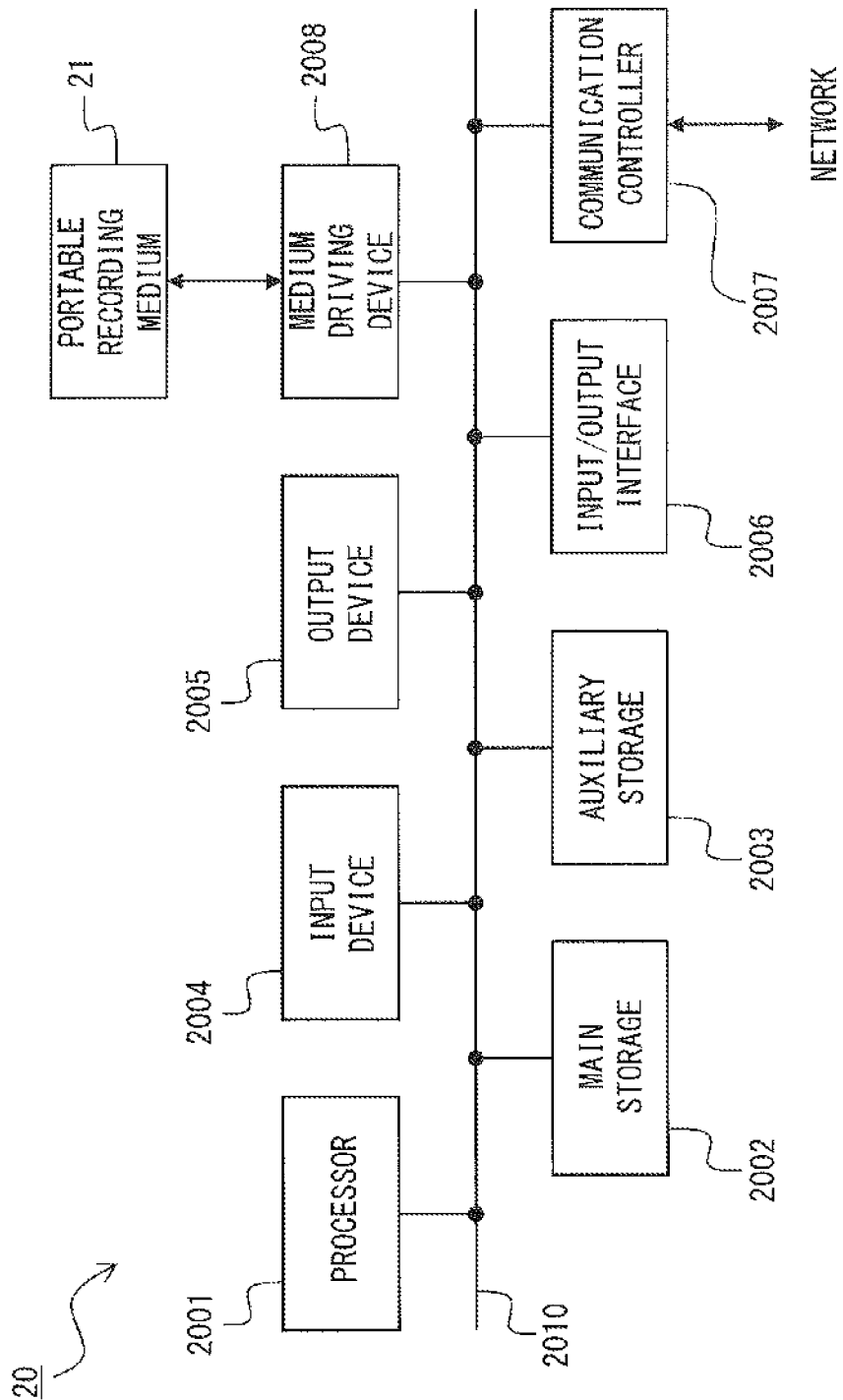
FIG. 11 illustrates a hardware configuration of a computer.

FIG. 11 illustrates a hardware configuration of a computer.

As illustrated in FIG. 11, a computer 20 includes a processor 2001, a main storage 2002, an auxiliary storage 2003, an input device 2004, an output device 2005, an input/output interface 2006, a communication controller 2007, and a medium driving device 2008. These components 2001 to 2008 in the computer 20 are connected to one another through a bus 2010, which makes it possible to perform transmission and reception of data between the components.

The processor 2001 is, for example, a central processing unit (CPU) or a micro processing unit (MPU). The processor 2001 executes various programs including an operating system, so as to control an entire operation of the computer 20. Further, the processor 2001 performs, for example, each of the processes illustrated in FIGS. 4A, 4B, 5A, and 5B.

The main storage 2002 includes a read only memory (ROM) and a random access memory (RAM) (not illustrated). For example, the ROM of the main storage 2002 has stored, for example, a specified basic control program that is read by the processor 2001 when the computer 20 starts. The RAM of the main storage 2002 is used by the processor 2001 as a working storage region as needed when the processor 2001 executes various programs. The RAM of the main storage 2002 can be used to store, for example, an image obtained from the image-capturing device 6, location information on a reference point in a face area extracted from an image, location information and feature information on a candidate corneal reflection, a movement range of a corneal reflection, and a movement vector $V_M$ of candidate corneal reflections.

The auxiliary storage 2003 is a storage that has a higher capacity than the RAM of the main storage 2002, such as a hard disk drive (HDD), or a non-volatile memory (solid state drive (SSD)) such as a flash memory. The auxiliary storage 2003 can be used to store, for example, various programs executed by the processor 2001 and a variety of data. The auxiliary storage 2003 can be used to store, for example, a program that includes, for example, each of the processes illustrated in FIGS. 4A, 4B, 5A, and 5B. Further, the auxiliary storage 2003 can be used to store, for example, an image obtained from the image-capturing device 6, location information on a reference point in a face area extracted from an image, location information and feature information on a candidate corneal reflection, a movement range of a corneal reflection, a movement vector $V_M$ of candidate corneal reflections, and a detected line of sight (the line-of-sight history 750).

The input device 2004 is, for example, a keyboard or a touch panel. When an operator (a user) of the computer 20 performs a specified manipulation on the input device 2004, the input device 2004 transmits input information associated with a content of the manipulation to the processor 2001. The input device 2004 can be used to input, for example, an instruction to start line-of-sight detection processing, an instruction to terminate the line-of-sight detection processing, and an instruction related to other processing that is executable by the computer 20, or to input, for example, various set values.

The output device 2005 includes, for example, a device such as a liquid crystal display device, and an audio playback device such as a speaker. The display device in the output device 2005 can be used as the display device 2 of the line-of-sight detection system 1 illustrated in FIG. 1.

The input/output interface 2006 connects the computer 20 to, for example, another electronic device. The input/output interface 2006 is equipped with, for example, a universal serial bus (USB) standard connector. The input/output interface 2006 can be used to connect the computer 20 to, for example, the image-capturing device 6 and the infrared light source 5.

The communication controller 2007 is a device that connects the computer 20 to a communication network such as the Internet and controls various communications performed between the computer 20 and another electronic device through the communication network. For example, the communication controller 2007 can be used to perform a communication between the computer 20 and, for example, a server in which various videos or the like to be displayed on the display device 2 are accumulated.

The medium driving device 2008 reads a program or data that is recorded in a portable recording medium 21, and writes data or the like stored in the auxiliary storage 2003 into the portable recording medium 21. For example, a reader/writer for a memory card that is compatible with one or more types of standards can be used as the medium driving device 2008. For example, when the reader/writer for a memory card is used as the medium driving device 2008, a memory card (a flash memory) of a standard with which the reader/writer for a memory card is compatible, such as a secure digital (SD) standard memory card, can be used as the portable recording medium 21. Further, a flash memory that is equipped with a USB standard connector can be used as the portable recording medium 21. Furthermore, when the computer 20 is provided with an optical disk drive that can be used as the medium driving device 2008, various optical disks recognizable by the optical disk drive can be used as the portable recording medium 21. A compact disc (CD), a digital versatile disc (DVD), and a Blu-ray Disc™ are examples of the optical disk that can be used as the portable recording medium 21. The portable recording medium 21 can be used to store, for example, a program that includes the processes illustrated in FIGS. 4A, 4B, 5A, and 5B, an image captured by the image-capturing device 6, and a history of a line of sight calculated (detected) by the computer 20.

When an instruction to start the processing illustrated in FIGS. 4A and 4B is input to the computer 20, the processor 2001 reads a line-of-sight program that includes the processing illustrated in FIGS. 4A and 4B and that is stored in a non-transitory recording medium such as the auxiliary storage 2003, so as to execute the program. During the execution of the line-of-sight program, the processor 2001 serves (operates) as the image obtaining unit 710, the area extracting unit 721, the corneal reflection extracting unit 722, the pupil extracting unit 723, the line-of-sight calculator 730, and the output unit 740 in the line-of-sight detection device 7 of FIG. 2. Further, for example, the RAM of the main storage 2002 and the auxiliary storage 2003 serve as a buffer (not illustrated), as well as the extracted information retaining unit 724 in the line-of-sight detection device 7 of FIG. 2, and a storage that stores the line-of-sight history 750.

The computer 20 that is operated as the line-of-sight detection device 7 does not necessarily include all of the components 2001 to 2008 of FIG. 11, and some of the components can be omitted according to the applications or the requirements. For example, the computer 20 may have a configuration in which the communication controller 2007 and the medium driving device 2008 have been omitted.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A line-of-sight detection device comprising:
a memory configured to store an image of a person that includes eyes of the person; and
a processor configured to detect a line of sight of the person on the basis of the image stored in the memory, wherein
the detecting the line of sight of the person includes:
extracting a candidate corneal reflection having a specified feature from a first image and from a second image captured after the first image is captured;
extracting a reference point on the person from the first image and from the second image;
calculating a threshold vector on the basis of a movement vector of the reference point and a predetermined threshold, wherein the movement vector has a start point at a location, in the second image, that overlaps the reference point in the first image and an endpoint at the reference point in the second image, and the threshold vector has a start point at a candidate location, in the second image, that overlaps a location of the candidate corneal reflection in the first image;
calculating a movement vector of a reflection location that has a start point at the candidate location in the second image and an endpoint at a location of the candidate corneal reflection extracted from the second image, and identifying, on the basis of the threshold vector and the movement vector of the reflection location, a corneal reflection from among a plurality of candidate corneal reflections extracted from the second image so as to identify a location of the corneal reflection;
extracting a location of a pupil from the image; and
calculating the line of sight of the person in the image on the basis of the identified location of the corneal reflection and the extracted location of the pupil.

2. The line-of-sight detection device according to claim 1, wherein
the calculating the threshold vector calculates the threshold vector that is a shortest distance from the candidate location to a movement range of an eye of the person in the second image, on the basis of a location of the end point of the movement vector of the reference point when the start point of the movement vector is the candidate location in the second image and on the basis of the movement range of the eye of the person.

3. The line-of-sight detection device according to claim 2, wherein
the identifying the location of the corneal reflection selects a set of the first image and the second image in which a size of the movement vector of the reference point is greater than a size of the threshold vector, and identifies the location of the corneal reflection.

4. The line-of-sight detection device according to claim 1, wherein
the extracting the reference point extracts a specified point on glasses worn by the person from the image as the reference point.

5. The line-of-sight detection device according to claim 1, wherein
the extracting the reference point extracts an eyebrow of the person from the image as the reference point.

6. The line-of-sight detection device according to claim 2, wherein the detecting the line of sight of the person further includes retaining a maximum value of the movement range of the eye of the person, wherein
the calculating the threshold vector calculates the threshold vector on the basis of a location of the end point of the movement vector of the reference point when the start point of the movement vector is the candidate location in the second image and on the basis of the maximum value of the movement range of the eye of the person.

7. The line-of-sight detection device according to claim 1, wherein
the calculating the line of sight calculates the line of sight of the person when there exist a plurality of the identified corneal reflections, on the basis of a location of a corneal reflection situated closest to the pupil among the plurality of the identified corneal reflections and on the basis of the location of the pupil.

8. A line-of-sight detection method comprising:
identifying, by a computer, a location of a corneal reflection from an image of a person that includes eyes of the person and extracting, by the computer, a location of a pupil from the image; and
calculating, by the computer, a line of sight of the person in the image on the basis of the identified location of the corneal reflection and the extracted location of the pupil, wherein
the identifying the location of the corneal reflection includes:
  extracting, by the computer, a reference point on the person from the image and extracting, by the computer, a candidate corneal reflection having a specified feature from the image;
  calculating, by the computer, a movement vector of the reference point that has a start point at a location, in a second image, that overlaps the reference point in a first image and an end point at the reference point in the second image, the second image being captured after the first image is captured in a plurality of the images;
  calculating, by the computer and on the basis of the movement vector of the reference point and a predetermined threshold, a threshold vector that has a start point at a candidate location, in the second image, that overlaps a location of the candidate corneal reflection in the first image, and calculating, by the computer, a movement vector of a reflection location that has a start point at the candidate location in the second image and an end point at a location of the candidate corneal reflection extracted from the second image; and
  identifying, by the computer and on the basis of the threshold vector and the movement vector of the reflection location, a corneal reflection from among a plurality of candidate corneal reflections extracted from the second image so as to identify a location of the corneal reflection.

9. The line-of-sight detection method according to claim 8, wherein
the calculating the threshold vector calculates, by the computer, the threshold vector that is a shortest distance from the candidate location to a movement range of an eye of the person in the second image, on the basis of a location of the end point of the movement vector of the reference point when the start point of the movement vector is the candidate location in the second image and on the basis of the movement range of the eye of the person.

10. The line-of-sight detection method according to claim 9, wherein
the identifying the location of the corneal reflection selects, by the computer, a set of the first image and the second image in which a size of the movement vector of the reference point is greater than a size of the threshold vector and identifies, by the computer, the location of the corneal reflection.

11. The line-of-sight detection method according to claim 8, wherein
the extracting the reference point extracts, by the computer, a specified point on glasses worn by the person from the image as the reference point.

12. The line-of-sight detection method according to claim 8, wherein
the extracting the reference point extracts, by the computer, an eyebrow of the person from the image as the reference point.

13. The line-of-sight detection method according to claim 9, wherein
the calculating the threshold vector reads, by the computer, a maximum value of the movement range of the eye of the person that is stored in a memory of the computer, and calculates, by the computer, the threshold vector on the basis of a location of the end point of the movement vector of the reference point when the start point of the movement vector is the candidate location in the second image and on the basis of the maximum value of the movement range of the eye of the person.

14. The line-of-sight detection method according to claim 8, wherein
when there exist a plurality of the identified corneal reflections, the calculating the line of sight of the person calculates the line of sight of the person on the basis of a location of a corneal reflection situated closest to the pupil among the plurality of the identified corneal reflections and on the basis of the location of the pupil.

15. A non-transitory computer-readable recording medium having stored therein a line-of-sight detection program that causes a computer to execute a process for detecting a line of sight of a person from an image, the process comprising:

identifying a location of a corneal reflection from an image of a person that includes eyes of the person and extracting a location of a pupil from the image; and calculating a line of sight of the person in the image on the basis of the identified location of the corneal reflection and the extracted location of the pupil, wherein the identifying the location of the corneal reflection includes:

extracting a reference point on the person from the image and extracting a candidate corneal reflection having a specified feature from the image;

calculating a movement vector of the reference point that has a start point at a location, in a second image, that overlaps the reference point in a first image from among a plurality of the images and an end point at the reference point in the second image, the second image being captured after the first image is captured in a plurality of the images;

calculating, on the basis of the movement vector of the reference point and a predetermined threshold, a threshold vector that has a start point at a candidate location, in the second image, that overlaps a location of the candidate corneal reflection in the first image, and calculating a movement vector of a reflection location that has a start point at the candidate location in the second image and an end point at a location of the candidate corneal reflection extracted from the second image; and identifying, on the basis of the threshold vector and the movement vector of the reflection location, a corneal reflection from among a plurality of candidate corneal reflections extracted from the second image so as to identify a location of the corneal reflection.

* * * * *